(12) United States Patent
Carrillo

(10) Patent No.: US 6,671,543 B1
(45) Date of Patent: Dec. 30, 2003

(54) SYSTEM AND METHOD FOR DETECTING WHETHER A PERSON IS UNDER THE INFLUENCE OF A PSYCHOTROPIC SUBSTANCE

(75) Inventor: Hipolito Carrillo, Guaynabo, PR (US)

(73) Assignee: EIS Technologies, Inc., Springfield, MA (US)

(*) Notice: Subject to any disclaimer, the term of this patent is extended or adjusted under 35 U.S.C. 154(b) by 97 days.

(21) Appl. No.: 10/034,557

(22) Filed: Oct. 19, 2001

Related U.S. Application Data

(60) Provisional application No. 60/241,637, filed on Oct. 19, 2000.

(51) Int. Cl.[7] .................................................. A61B 5/04
(52) U.S. Cl. ........................ 600/544; 600/545; 600/300
(58) Field of Search ................................. 600/300, 544, 600/545; 128/920, 923

(56) References Cited

U.S. PATENT DOCUMENTS

| 4,417,592 A | * | 11/1983 | John ........................... 600/544 |
| 5,813,993 A | * | 9/1998 | Kaplan et al. ............... 600/544 |
| 5,995,868 A | * | 11/1999 | Dorfmeister et al. ........ 600/544 |
| 6,496,724 B1 | * | 12/2002 | Levendowski et al. ...... 600/544 |
| 2001/0020137 A1 | * | 9/2001 | Granger ....................... 600/544 |

* cited by examiner

Primary Examiner—Max F. Hindenburg
Assistant Examiner—Jonathan Foreman
(74) Attorney, Agent, or Firm—Samuels Gauthier & Stevens

(57) ABSTRACT

A system is disclosed for determining whether an equipment operator is under the influence of a psychotropic substance. The system includes an input unit for receiving signals from the subject regarding the frequencies of the subject's brain waves, and for producing raw sample data. The system also includes a processing unit for processing the raw sample data, and for producing evaluation data responsive to the raw sample data and responsive to pre-recorded threshold data. The system also includes a control unit for providing a pass/fail signal responsive to the evaluation data to be used to control equipment.

10 Claims, 4 Drawing Sheets

SYSTEM AND METHOD FOR DETECTING WHETHER A PERSON IS UNDER THE INFLUENCE OF A PSYCHOTROPIC SUBSTANCE

The present application claims priority to U.S. Provisional Application No. 60/241,637 filed on Oct. 19, 2000.

BACKGROUND OF THE INVENTION

The present invention relates to systems and methods for determining whether a person is intoxicated or otherwise under the influence of a psychotropic substance. The invention relates in particular, to systems for determining this through non-invasive means.

The dangers of having a person operate heavy machinery or operate a vehicle while under the influence of any psychotropic substance that may impede or otherwise impair that person's coordination or concentration are well known. Such a situation may present a risk to both the operator as well as anyone in the vicinity of the operator. Systems for detecting psychotropic substances in a person have generally focused on the detection of specific drugs in the person. For example, certain systems have been developed to facilitate the identification of whether an individual is intoxicated by alcohol (e.g., breathalizer systems), but these systems are not typically effective with respect to other drugs and psychotropic substances. Other systems have been developed to detect whether a person has certain chemicals in their system (e.g., marijuana) to determine whether that person has recently taken the drug, but again, such systems are not generally effective against all psychotropic substances.

There is a need, therefore, for a system and method for detecting whether a person is under the influence of a psychotropic substance.

SUMMARY OF THE INVENTION

The invention provides a system for determining whether an equipment operator is under the influence of a psychotropic substance. The system includes an input unit for receiving signals from the subject regarding the frequencies of the subject's brain waves, and for producing raw sample data. The system also includes a processing unit for processing the raw sample data, and for producing evaluation data responsive to the raw sample data and responsive to pre-recorded threshold data. The system also includes a control unit for providing a pass/fail signal responsive to the evaluation data to be used to control equipment.

BRIEF DESCRIPTION OF THE DRAWINGS

The following description may be further understood with reference to the accompanying drawing in which.

DETAILED DESCRIPTION OF THE INVENTION

Figure 1:
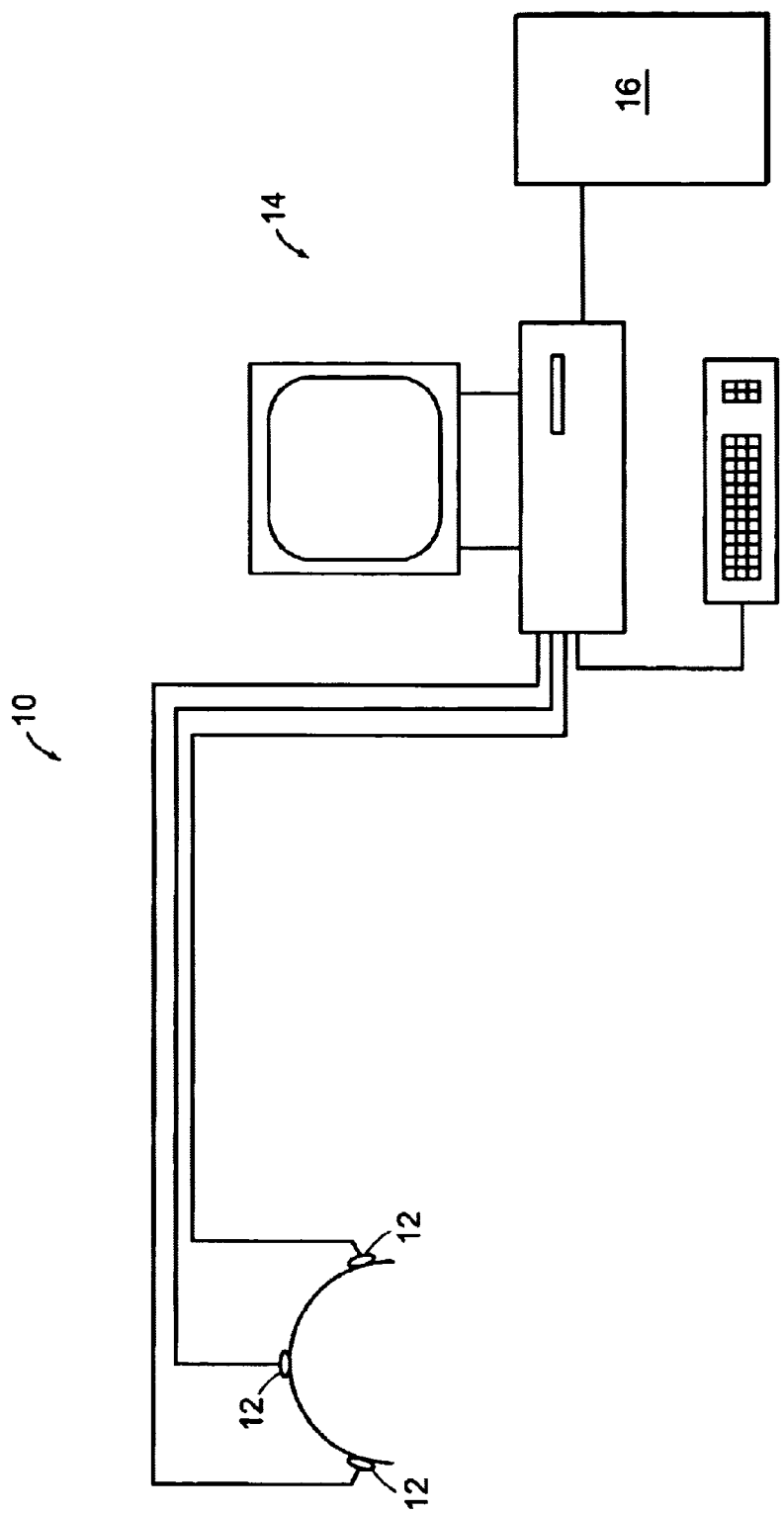
FIG. 1 shows an illustrative schematic representation of a system of the invention.

The invention provides an electronic system 10 for reading and detecting anomalies in brain waves of human beings using sensors 12 that are coupled to a computer system 14 that is in turn coupled to a data storage medium 16 as shown in FIG. 1. In particular, the invention provides for detecting when a particular person's brain waves are not within their normal range of frequencies.

The neuronal basis of human consciousness is associated with certain intermediate levels of brain wave frequency, which are characterized by desynchronized, waking brain frequency. The fact that a particular brain exhibits relatively little neuronal activity, may indicate that the person is under the influence of consciousness altering substances (e.g., anesthesia, benzodiazepines, barbiturics, cocaine), or is under the influence of a consciousness altering state (e,g., an epileptic attack). Such relatively low neuronal activity is inconsistent with the neuronal activity that occurs during consciousness.

When a person is awake and alert under normal conditions, their brain waves typically have frequencies in the range of about 14 Hz to about 30 Hz, and in particular are about 20 Hz. These waves are generally referred to as beta waves. Beta waves are typically irregular and vary in amplitude, phase and frequency. Traces of such waves tend to be desynchronized. Brain waves of different frequencies, however, may also be detected in a brain wave trace. For example, brain waves having frequencies of about 4 Hz–7 Hz may be detected, and waves having frequencies of about 0.3 Hz. to 3.5 Hz (also called delta waves) may also be detected. Brain waves in these frequency ranges typically occur in persons that are sleeping, are ill, or are under the influence of certain substances such as drugs or alcohol.

The invention provides a system that may detect any anomaly in the normal waking range of brain wave frequencies, and the presence of diseases or the use of alcohol or drugs in a subject may be detected. The detection of such anomalies in persons that had previously tested normal, may serve as a primary non-invasive tool for indicating the presence of normal or abnormal brainwaves.

Following testing, a test administrator may determine whether an individual with an abnormal brainwave should cease or stop working until further tests may be performed that might rule out the possibility of the presence of drugs or a medical condition in the person. The test administrator may also have the discretion to decide whether the person may return to their job or other activity. In various embodiments, the system may be attached to the control system of heavy machinery or vehicles, and may be programmed to detect fraud and require that certain individuals by personally identified.

Figure 2A:
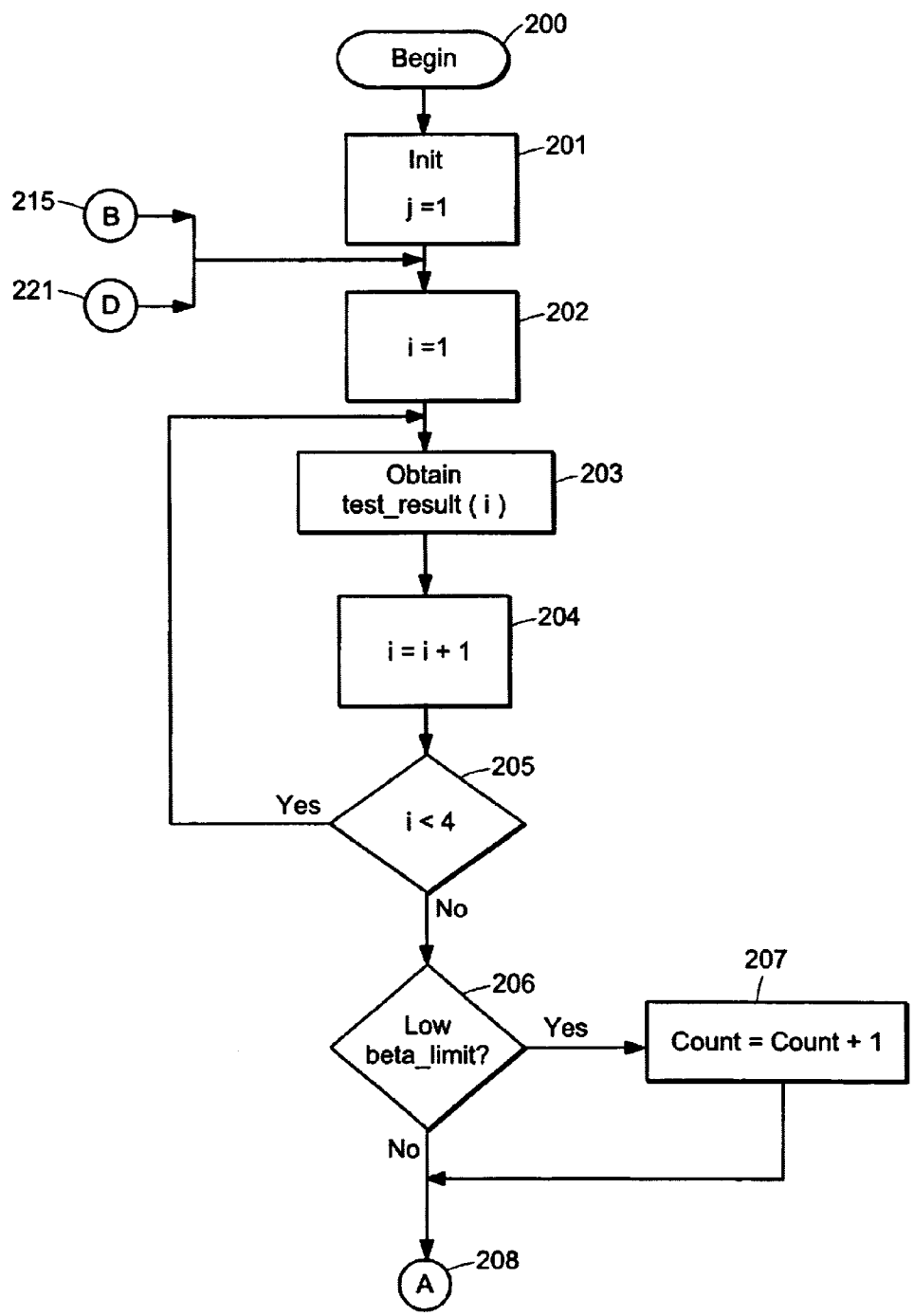
FIGS. 2A–2C show illustrative flow charts of the operation of a system of the invention.

As shown in FIGS. 2A, during operation, a system in accordance with an embodiment of the invention may begin (step 200) by initializing the system (step 201). The initialization step 201 involves instructing the user to clear the area of the subject to be tested, to apply the electrode sensors with any necessary ointment, to plug in the electrode sensors, and to turn on the data acquisition unit. This step also involves initializing several variables such as setting counters i, j and Fail_Counter to zero. The next step 202 involves setting the counter i to 1. The program then obtains the raw data from the subject for a single reading test result(i) (step 203). A set of readings is taken at that time by cycling through the step 203 a specified number of times (e.g., 3) as provided by steps 204 and 205. Specifically, step 204 increments the counter i, and the program returns to step 203. This continues until the counter i exceeds the specified limit (e.g., 4), at which time the program proceeds from step 205 to step 206.

Figure 2B:
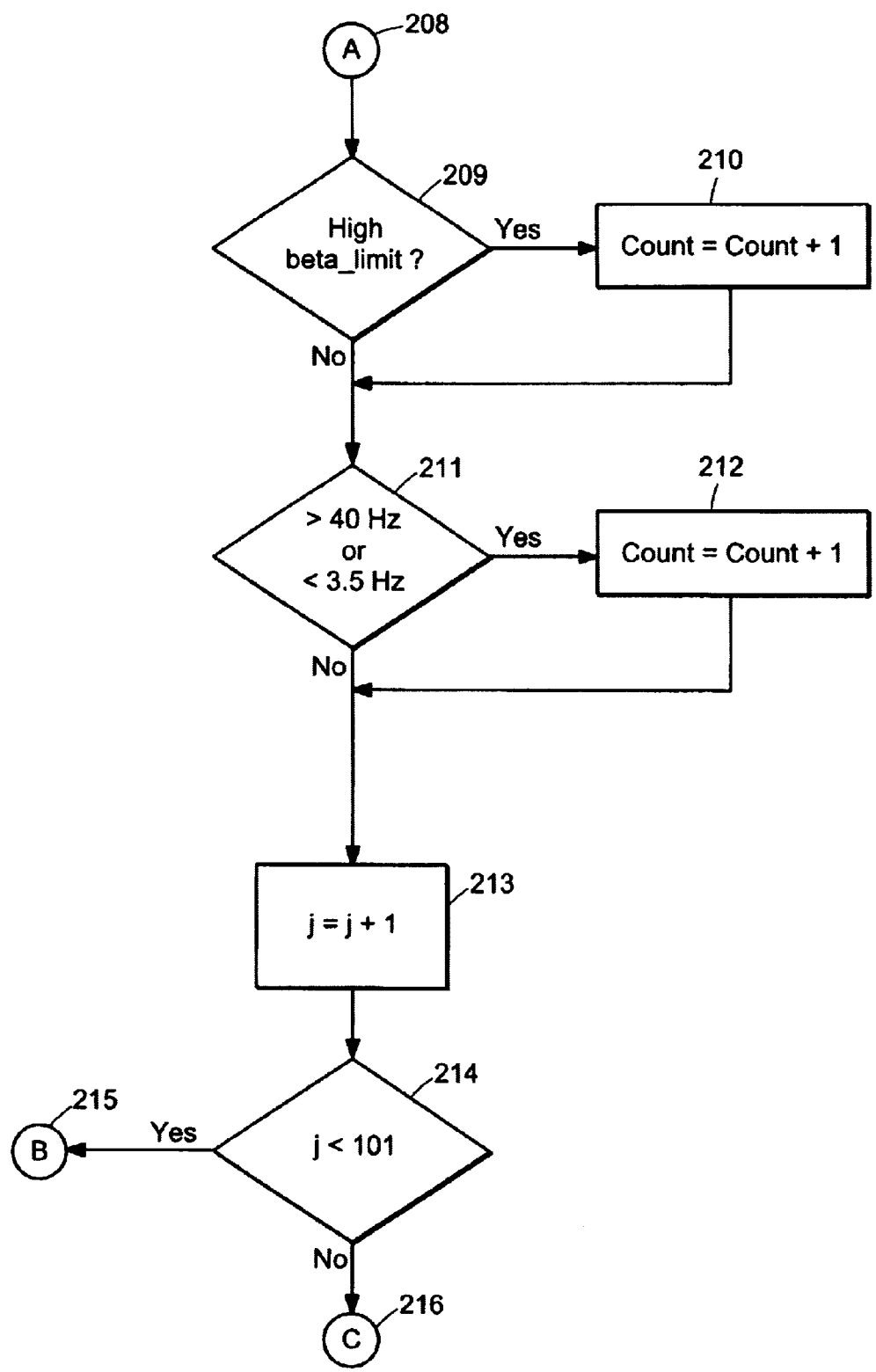

The set of raw data obtained as test_results(i) is then analyzed and checked against a low beta limit (step 206) and a high beta limit (step 209) shown in FIG. 2B. If the raw data exceeds either of these limits, then a fail_counter is incremented as indicated at steps 207 and 210. The step indicated at 208 advances to the drawing shown in FIG. 2B.

Figure 2C:
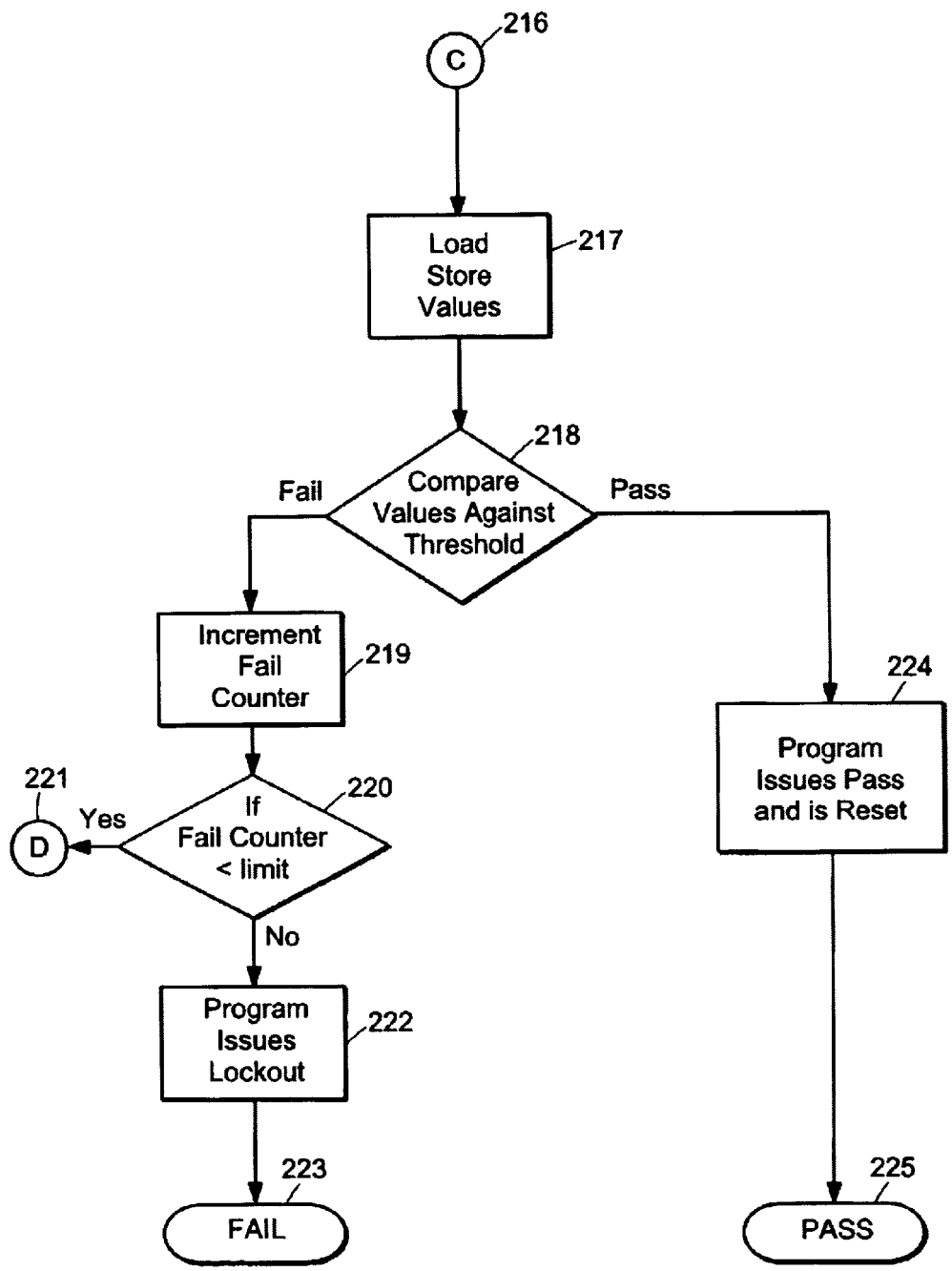

As further shown in FIG. 2B, a further check may be performed to determine whether the raw data exceeds a high check point (e.g., 40 Hz), or a very low check point (e.g., 3.5 Hz) as shown at step 211. If either of these conditions exist, then the fail_counter is further incremented (step 212). The cycle counter j is then incremented (step 213), and if the cycle counter is less than a predefined cycle limit (e.g., 101) as shown at step 214, then the program returns to step 202 as shown at transition step 215. Once the required number of sets of data are obtained (e.g., 100 sets), then the system may proceed (step 216) to further evaluate the data as shown in FIG. 2C. In other embodiments, the system may simply enter a pass or fail status based on the value of the fail_counter.

If further processing is desired, prerecorded data regarding normal brain wave activity for the subject is loaded (step 217), and the system compares the test data against the pre-recorded data as thresholds as shown in step 218. If the test fails, then a fail counter is incremented (step 219), and if the limit on the number of attempts has not yet been reached (step 220), then the system returns to acquire another set of data (step 221). If the limit on the fail counter has been reached, then the system issues a lockout (step 222), and the program ends with a failed status (step 223). If the values compare favorably with respect to the threshold values, then the system issues a pass notification and resets (step 224). The system then ends with a pass status (step 225).

The system may be coupled to the operating controls of heavy machinery of vehicles, and permit an operator to control the machinery or vehicle only if a pass status is obtained by the system.

Those skilled in the art will appreciate that numerous modifications and variations may be made to the above disclosed embodiments without departing from the spirit and scope of the invention.

What is claimed is:

1. A system for determining whether an equipment operator is under the influence of a psychotropic substance, said system comprising:

input means for receiving signals from a subject regarding the frequencies of the subject's brain waves, and for producing raw sample data;

processing means for processing said raw sample data, and for producing evaluation data responsive to said raw sample data and responsive to pre-recorded threshold data, said evaluation data being indicative of whether said raw sample data includes a signal having a frequency within the range of about 14 Hz to about 40 Hz; and control means for providing a pass/fail signal responsive to the evaluation data to be used to control equipment.

2. The system as claimed in claim 1, wherein said pre-recorded threshold data includes a lower limit that is about 14 Hz.

3. The system as claimed in claim 1, wherein said pre-recorded threshold data includes an upper limit that is about 30 Hz.

4. The system as claimed in claim 3, wherein said system further determines whether the raw data exceeds a critically high level.

5. The system as claimed in claim 4, wherein said critically high level is 40 Hz.

6. The system as claimed in claim 2, wherein said system further determines whether the raw data is below a critically low level.

7. The system as claimed in claim 6, wherein said critically low level is 3.5 Hz.

8. A system for determining whether an equipment operator is under the influence of a psychotropic substance, said system comprising:

electrode sensors for receiving brain wave signals from a subject regarding the frequencies of the subject's brain waves, and for producing a set of raw sample data;

an evaluation unit for determining a fail count based on the set of raw sample data, and for producing evaluation data representative of said fail count, said evaluation data being indicative of whether said brain wave signals from a subject include a signal having a frequency within the range of about 14 Hz to about 40 Hz; and control means for providing a pass/fail signal responsive to the evaluation data to be used to control equipment.

9. The system as claimed in claim 8, wherein said system further produces a plurality of sets of raw sample data.

10. A system for determining whether an equipment operator is under the influence of a psychotropic substance, said system comprising:

electrode sensors for receiving brain wave signals from a subject regarding the frequencies of the subject's brain waves, and for producing a set of three raw sample data points;

cycling means for obtaining a plurality of sets of three raw sample data points;

an evaluation unit for determining a fail count based on the plurality of sets of raw sample data, and for producing evaluation data representative of said fail count, said evaluation data being indicative of whether said raw sample data includes a signal having a frequency within the range of about 14 Hz to about 40 Hz; and control means for providing a pass/fail signal responsive to the evaluation data to be used to control equipment.

* * * * *